United States Patent [19]

Mizuta

[11] Patent Number: 4,941,741
[45] Date of Patent: Jul. 17, 1990

[54] OPHTHALMIC DISEASE DETECTION APPARATUS

[75] Inventor: Susumu Mizuta, Tokyo, Japan

[73] Assignee: Kowa Company, Ltd., Japan

[21] Appl. No.: 216,385

[22] Filed: Jul. 7, 1988

[30] Foreign Application Priority Data

Jul. 15, 1987 [JP] Japan ................... 62-174951

[51] Int. Cl.$^5$ ............................. A61B 3/10
[52] U.S. Cl. ...................... 351/221; 351/205; 351/214
[58] Field of Search .............. 351/205, 214, 221; 128/303.1, 745

[56] References Cited

U.S. PATENT DOCUMENTS 4,213,678  7/1980  Pomerantzeff ................ 351/221

Primary Examiner—Rodney B. Bovernick
Attorney, Agent, or Firm—Bruce L. Adams; Van C. Wilks

[57] ABSTRACT

An apparatus for detecting ophthalmic diseases, such as inflammation in a patient's eye, includes a projection system for projecting and focusing a laser beam at a selected spot in the eye. The laser light scattered from the eye is photoelectrically detected through a slit in a mask and converted into an electrical signal which is used to determine the protein concentration in the patient's eye. A light shield member is displaceable in front of the mask slit to selectively block diffused light from the eye or scattered laser light to improve the S/N ratio of the electrical signal.

12 Claims, 3 Drawing Sheets

OPHTHALMIC DISEASE DETECTION APPARATUS

BACKGROUND OF THE INVENTION

1. Field of the Invention

This invention relates to an apparatus for detecting ophthalmic diseases in a patient's eye, and more particularly to an apparatus for detecting ophthalmic diseases in which laser light is radiated via an optical system at one spot in the camera oculi of the patient's eye, particularly in the anterior chamber thereof, and the laser light scattered therefrom is analyzed to measure the protein concentration for ophthalmic disease detection in the camera oculi.

2. Description of the Prior Art

The camera oculi is comprised of the camera oculi anterior (anterior chamber) and the camera oculi posterior (posterior chamber). The camera oculi anterior is defined by a space surrounded by the rear surface of the cornea, a part of the ciliary body, the iris, and the front surface of the crystalline lens, while the camera oculi posterior is defined by a space surrounded by the rear surface of the iris, the inner surface of the ciliary body, and the front surface of the crystalline lens. The camera oculi is filled with transparent humor aqueous, which has chemical and physical characteristics that are different from those of lymphatic liquid and closely related to the metabolism of the cornea or crystalline lens. The humor aqueous contains proteins the increase of which causes turbidity in the camera oculi when it becomes inflamed.

In this respect, the measurement of protein concentration in the camera oculi of the patient's eye is of great importance in determining whether the camera oculi is inflamed, that is, whether a blood-aqueous barrier functioning normally or not.

To measure the protein concentration in the camera oculi, a slit lamp microscope is very often used to determine the turbidity by grading via the naked eye. This is, however, disadvantageous because the judgment depends upon the person who performs the measurement.

On the other hand, a photographic measuring method has been developed to make a quantitative measurement of the protein concentration. This method is, however, highly complicated to analyze, and is thus very difficult to apply in a clinical examination.

To overcome this problem, an apparatus for detecting ophthalmic diseases has been proposed which includes means for focusing a laser beam at a selected spot in the camera oculi of an eye. In the apparatus, the light scattered from the eye is photoelectrically detected and converted into an electrical signal which is subsequently used to determine the protein concentration essential to ophthalmic disease detection in the camera oculi of the patient's eye. See, for example, Japanese Patent Laying-open No. 120834/87.

In apparatuses found in the prior art, light laterally scattered from the eye is detected after passing through a mask having a slit to limit the scattered light that impinges on the mask. In these apparatuses, the scattered light from the laser beam and the diffused light from eye organs such as the crystalline lens, vitreous humor, retina, implanted artificial crystalline lens, etc. are simultaneously observed, resulting in a degraded S/N ratio and poor measurement accuracy.

SUMMARY OF THE INVENTION

It is therefore an object of the present invention to provide an apparatus for detecting ophthalmic diseases in a patient's eye which is capable of measuring diseases in the eye precisely and easily.

Another object of the present invention is to provide an apparatus for detecting ophthalmic diseases which enable the noise from diffused light from the eye or reflected or scattered light which may impinge on the spot to be measured in the patient's eye to be reduced or removed.

An apparatus for detecting ophthalmic diseases according to the present invention comprises a laser source for producing a laser beam, a laser beam projector for projecting the laser beam, means for focusing the laser beam at a selected spot in the patient's eye, means for receiving light scattered from the patient's eye and photoelectrically converting it into an electrical signal, a mask disposed in front of the photoelectric converting means and formed thereon with a slit having a predetermined width to limit the scattered light that impinges on the photoelectric converting means, light shield means provided in the slit for blocking the diffused light from the eye or scattered light from the laser beam impinging on the spot in the patient's eye, and means for processing the electrical signal to evaluate ophthalmic diseases in the patient's eye.

As stated in the above, on the aperture in the slit scattered light from the laser beam and diffused light from the various organs in the eye may be observed. In accordance with the present invention, a light shield member is provided in the slit to block the diffused light from the eye. This makes it possible to increase the effective signal that is, the scattered light component of light scattered from the eye and to reduce the noise due to diffused light from the eye, thus improving the overall S/N ratio and measurement accuracy.

Preferably, the light shield member is constructed as a line-shaped stop extending parallel to the laser beam, and is displaceable within the slit perpendicularly to the direction along which the shield member extends.

BRIEF DESCRIPTION OF THE DRAWINGS

The objects and features of the present invention will become more apparent from a consideration of the following detailed description taken in conjunction with the accompanying drawings in which.

DETAILED DESCRIPTION OF THE PREFERRED EMBODIMENTS

The invention will now be described in detail with reference to the drawings.

Figure 1:
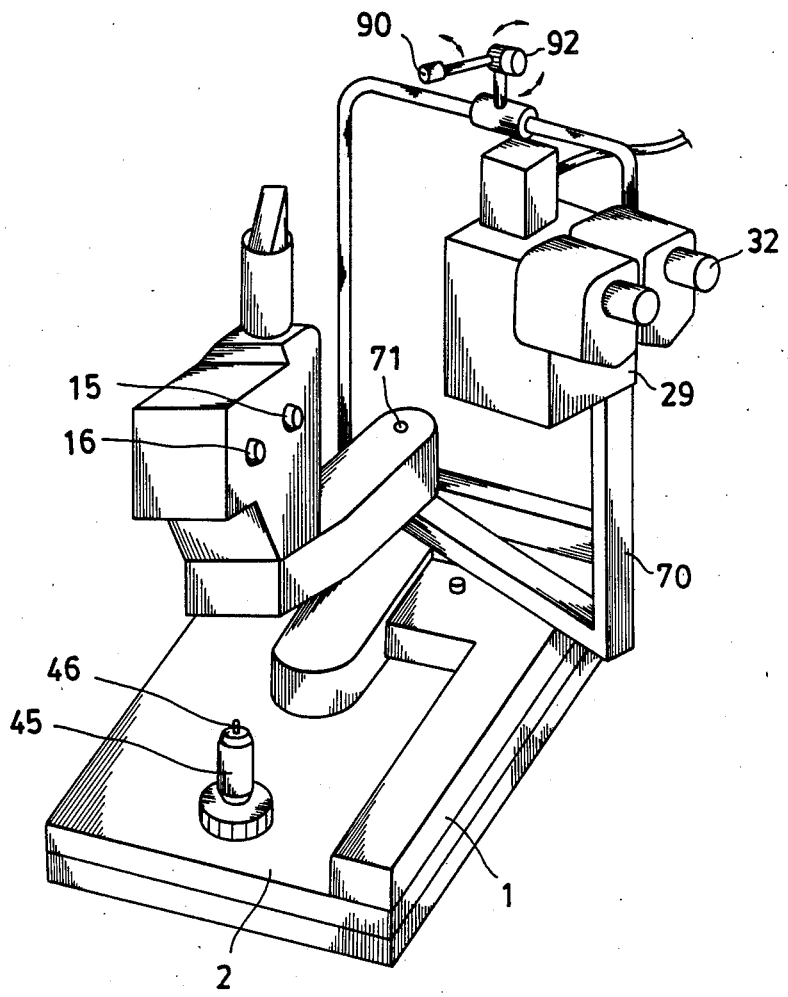
FIG. 1 is a perspective view of an apparatus according to the present invention.
Figure 2:
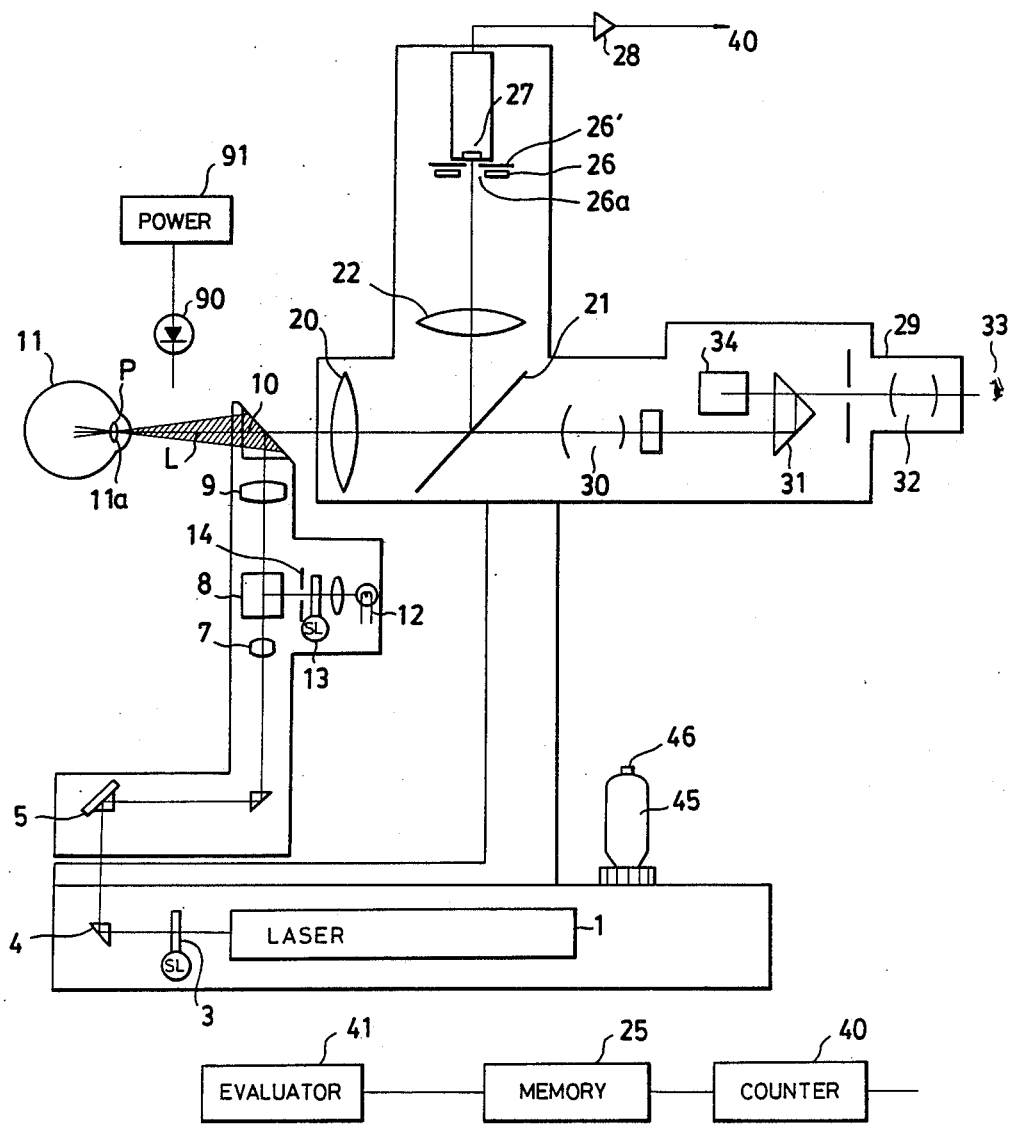
FIG. 2 is an illustrative view showing the arrangement of the optical system of the apparatus.

In FIGS. 1 and 2, which show an arrangement of the ophthalmic disease detection apparatus according to the present invention, reference numeral 1 denotes a laser light source, such as, for example, a helium-neon or argon laser source. The laser light source 1 is disposed on a stand 2. Light from the laser light source 1 is passed through a laser beam filter 3 and via a prism 4, prisms 5 and 6, a lens 7, a beam splitter 8, a condenser lens 9 and a prism 10 to converge on the eye under examination 11 at a spot in an anterior chamber 11a thereof.

The laser beam projector is provided with a slit light source 12. Light from the slit light source 12 passes via a slit light shutter 13 and a slit 14 and goes via the beam splitter 8, lens g and prism 10 to form a slit image on the anterior chamber 11a. With the light from the laser light source being converged to a spot, this slit image is for illuminating the surrounding area to facilitate confirmation of the position of the spot of converged light.

The width and length of the slit 14 can be adjusted by an adjusting knob 15 and a switching knob 16, respectively, which are shown in FIG. 1.

A portion of the laser light scattered from the measuring spot in the anterior chamber 11a passes through an objective lens 20 of a detection section 29 and is split by a semitransparent mirror or beam splitter 21. One part of the light thus split passes through a lens 22, light-shielding means comprising a mask 26 provided with a slit 26a and a shutter 26′ and impinges on a photomultiplier 27 used as the photoelectric converter. The other part of the scattered light split by the beam splitter 21 passes via a lens 30 and prisms 31 and 34 to an eyepiece 32 by means of which an examiner 33 can carry out observations.

The output from the photomultiplier 27 is passed through an amplifier 28 and is fed to a counter 40 and the intensity of the scattered light detected by the photomultiplier is counted as numbers of pulses per unit time period. The output of the counter 40, i.e., the number of samplings or the total pulse count, is stored in a memory 25 allocated for each unit time period. The data stored in the memory 25 is processed by an evaluating device 41 which, as explained below, computes the concentration of protein in the anterior chamber on the basis of the count value stored in the memory 25.

The detector 29 is affixed to a support 70. The support 70 and the laser beam projector are provided so as to be rotatable, with respect to each other, about a spindle 71, so as to allow the angle between the optical axes of the laser beam projector and the light receiving means to be adjusted to the required setting. In the preferred embodiment, detection is carried out with this angle set at about 90 degrees.

Figure 3:
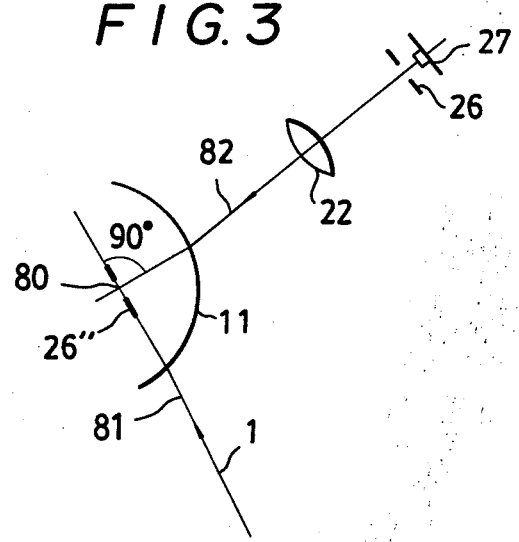
FIG. 3 is an illustrative view showing the arrangement of the optical axes of a laser projector and light receiving portion.

Thus in accordance with this embodiment, as illustrated in FIG. 3 the light receiving means and the laser beam projector are disposed so that their optical axes cross at around 90 degrees. At this time an image 26″ of the mask formed by the lens in the light receiving means is formed at the beam waist 80 on the optical axis of the light receiving means at a position which is a conjugate with that of the mask.

Figure 4:
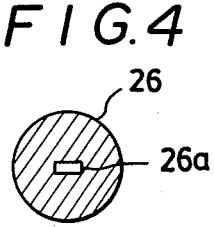
FIG. 4 is an illustrative view showing the configuration of a mask.
Figure 5:
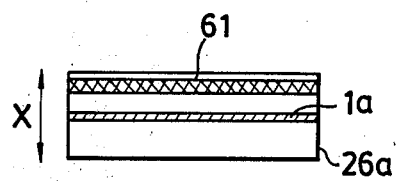
FIG. 5 is an illustrative view showing the detailed configuration of a mask with a light shield member.
Figure 6:
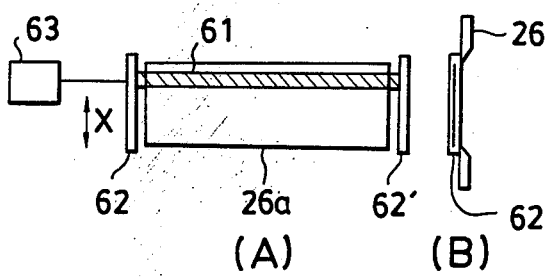
FIGS. 6 (A) and 6(B) are plan and side views each showing a driving mechanism for the light shield member.

FIGS. 4 and 5 show the slit 26a of the mask 26 provided with a light shield member 61 for blocking light diffusing from the eye. The shield member 61 is constituted as a line-shaped stop that is several times thicker than an image 1a of the received laser beam, and as illustrated by FIG. 6, it can be driven, for example by a motor 63, along side rails 62, 62′ to scan in a direction perpendicular to the laser beam 1a.

In accordance with this invention, an eye fixation light 90 comprising a light-emitting diode or the like powered by electricity supplied from a power source 91 is disposed at a position that permits the examiner to fix the patient's eye. The light selected for the eye fixation light 90 is of a different color than the light of the laser light source 1. For example, when the light from the laser light source is red, a green light is selected. The eye fixation light 90 can be turned in the direction indicated by the arrow by means of a link mechanism 92 to enable it to be adjusted so that it is always in an optimum position with respect to the patient's eye. Provided on the base 2 is an input means, such as a joystick 45 equipped with a push-button 46, and this can be operated to insert the laser filter 3, the slit light shutter 13 and the photomultiplier shutter 26′ into, or retract the said elements from, the respective optical system.

The operation of the apparatus will now be described. In conducting the measurement, the slit light source 12 is activated and an image of the slit 14 is formed, via the beam splitters 8 and 10 and the lens 9 on a part of the anterior chamber 11a that includes the measurement point P. Following this, light from the laser light source 1 is converged on the measuring point P via the said optical system.

A portion of the light from the measuring point P is simultaneously directed by the beam splitter 21 to the examiner 33 for observation and through a lens 22, a prism (not shown) and the mask 26 to impinge on the photomultiplier 27.

In the measurement the receiving means can operate in two modes. The first mode operates to include the scattered light and the second operates to exclude the scattered light. The shield member 61 is scanned from the upper edge of the aperture slit to the lower edge (i.e., in the direction denoted by X in FIG. 5). When the shield member 61 is in a first position in the vicinity of the upper edge of the aperture slit, scattered laser light and light diffusing within the eye is observed and the intensity $I_v$ of the sum of this light is measured (first mode). When the shield member 61 is in a second position in the central part of the slit, scattered laser light is blocked, only light diffused from within the eye is observed and the intensity of the light $I_c$ is measured (second mode). When the shield member 61 is in a third position in the vicinity of the lower edge of the slit, again scattered laser light is observed and the intensity $I_d$ of light diffusing from within the eye is measured (first mode). Therefore, the intensity $I_s$ of the scattered laser light can be obtained by deducting $I_c$ from the arithmetic mean of $I_v$ and $I_d$.

$$I_s = \frac{I_v + I_d}{2} - I_c \tag{1}$$

The photoelectric converter 27 receives light via the slit 26a and converts the light into a corresponding series of pulses which are counted by the counter 40 as numbers of pulses per unit time and the count values are stored in the memory 25 allocated for each unit time period. The evaluating device 41 processes the data contained in the memory 25, and uses equation (1) to calculate the protein concentration in the anterior chamber.

When the line-shaped stop is not scanning, the stop acts as a shield member to block light diffusing from within the eye, increasing the precision of the measurement of protein in the anterior chamber.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

I claim:

1. An apparatus for detecting ophthalmic diseases in a patient's eye comprising:
    a laser source for producing a laser beam;
    a laser beam projector for projecting the laser beam;
    means for focusing the laser beam at a selected spot in the patient'eye;
    means for receiving light scattered from the patient's eye and photoelectrically converting it into an electrical signal;
    a mask disposed in the front of said photoelectric converting means and formed thereon with a slit having predetermined width to limit the scattered light that impinges on said photoelectric converting means;
    light shield means for blocking the light scattered from the eye, the light shield means being disposed in the slit to be displaceable so as to shield the light scattered from the selected spot in the eye to extract noise corresponding to light other than the light scattered from the selected spot in the eye; and
    means for processing the electrical signal derived from the light scattered from the eye with the noise removed therefrom to evaluate for opthalmic diseases in the patient's eye.

2. An apparatus as set forth in claim 1, wherein said light shield means is constructed as a line-shaped stop several times thicker than an image of said laser beam formed on said slit.

3. An apparatus as set forth in claim 1, wherein said light shield means is displaceable within said slit perpendicularly to a direction along which said light shield means extends.

4. An apparatus according to claim 1, wherein said light shield means shields the light scattered from the selected spot in the eye when it is in the central portion of the slit.

5. An apparatus for examining particles in a patient's eye comprising: means for projecting a laser beam at a selected spot in a patient's eye whereby laser light is scattered by particles at the selected spot in the patient's eye and light is diffused by other parts of the patient's eye; receiving means operable in a first mode to receive both the scattered laser light and diffused light from the patient's eye and photoelectrically convert the same into an electric signal proportional to the amount of received light and operable in a second mode to receive diffused light but not scattered laser light from the patient's eye and photoelectrically convert the same into an electric signal proportional to the amount of received light; and processing means for processing the electric signals to derive therefrom an output signal representative of a property of the particles at the selected spot in the patient's eye based on the scattered laser light.

6. An apparatus according to claim 5; wherein the receiving means includes a mask having a slit therein, the mask being positioned so that the scattered laser light and diffused light pass through the mask slit, and means for selectively blocking the passage of light through different areas of the mask slit to define the first and second modes.

7. An apparatus according to claim 7; wherein the means for selectively blocking the passage of light comprises a displaceable light-blocking member disposed across the mask slit, the light-blocking member having a width less than that of the mask slit and being displaceable widthwise across the mask slit, and means for displacing the light-blocking member in the widthwise direction across the mask slit.

8. An apparatus according to claim 7; wherein the receiving means includes means for directing the scattered laser light through the central portion of the mask slit, and the means for displacing the light-blocking member includes means for sequentially displacing the light-blocking member from one widthwise end position of the other widthwise end position of the mask slit so that the light-blocking member blocks the passage of scattered laser light only when at the central portion of the mask slit.

9. An apparatus according to claim 8; wherein the receiving means includes photoelectric converting means positioned downstream of the mask slit for receiving the light passing therethrough for converting the light into an electric signal.

10. An apparatus according to claim 6; wherein the receiving means includes photoelectric converting means positioned downstream of the mask slit for receiving the light passing therethrough for converting the light into an electric signal.

11. An apparatus according to claim 6; wherein the processing means includes means for processing the electric signals to derive therefrom an output signal representative of the concentration of the particles at the selected spot in the patient's eye.

12. An apparatus according to claim 5; wherein the processing means includes means for processing the electric signals to deprive therefrom an output signal representative of the concentration of the particles at the selected spot in the patient's eye.

* * * * *